United States Patent [19]

Anderson et al.

[11] Patent Number: 5,042,979
[45] Date of Patent: Aug. 27, 1991

[54] CLOSED LOOP SYSTEM FOR EMBRYO RETRIEVAL

[75] Inventors: Mark Anderson, R.R. 2, Elmwood, Wis. 54740; Cameron Eilts; Randy Winch, both of Fennimore, Wis.

[73] Assignee: Mark Anderson, Elmwood, Wis.

[21] Appl. No.: 512,470

[22] Filed: Apr. 23, 1990

[51] Int. Cl.⁵ .................. A61M 1/00; A61B 17/43
[52] U.S. Cl. ...................... 604/319; 600/34
[58] Field of Search ......... 604/317, 329, 21; 600/33, 34; 128/898, 899, 912; 210/194

[56] References Cited

U.S. PATENT DOCUMENTS

| | | | |
|---|---|---|---|
| 4,193,392 | 3/1980 | Barnett | 600/34 |
| 4,563,172 | 1/1986 | Ferguson | 600/34 |
| 4,781,706 | 11/1988 | Suzuhi et al. | 604/317 |
| 4,817,599 | 4/1989 | Drews | 604/27 |
| 4,824,434 | 4/1989 | Seitz, Jr. | 600/33 |

FOREIGN PATENT DOCUMENTS

| | | | |
|---|---|---|---|
| 0254410 | 1/1988 | European Pat. Off. | 604/37 |
| 3605384 | 8/1987 | Fed. Rep. of Germany | 600/33 |
| 8200754 | 3/1982 | World Int. Prop. O. | 600/34 |

*Primary Examiner*—Randall L. Green
*Assistant Examiner*—Robert Clarke
*Attorney, Agent, or Firm*—Edward H. Loveman

[57] ABSTRACT

A system for embryo retrieval from a uterine cavity may employ apparatus comprising a container of liquid medium, a syringe and a filter interconnected by a plurality of valved conduits connected in a closed loop to circulate the liquid medium into and out of the container, syringe, filter and cavity cyclically. The circulation cycle can be repeated many times with a minimum amount of liquid medium to collect a maximum number of embryos in the filter.

12 Claims, 2 Drawing Sheets

CLOSED LOOP SYSTEM FOR EMBRYO RETRIEVAL

BACKGROUND OF THE INVENTION

1. Field of the Invention

This invention concerns an improved embryo retrieval system for use in collecting embryos of various mammalian species, and involves both a new method and a new apparatus for efficiently retrieving embryos from an animal.

2. Description of the Prior Art

Heretofore it has been conventional for a veterinarian to use several liters of a specially prepared liquid solution to flush the uterus of an animal for collecting any embryos lodged therein. The flushing liquid containing one or more embryos is drained out into a separate receptacle, and this procedure must then be repeated to insure that all of the embryos have been retrieved. This generally practiced method is slow, laborious, and complicated and considerable professional skill is required to perform the embryo collecting procedure. A great disadvantage is the possibility of contamination of the liquid medium when large volumes thereof are used. The prior method for retrieval of embryos is costly in use of professional time, and in consumption of expensive materials and equipment and it is generally inefficient, frequently resulting in loss of many sought after embryos.

SUMMARY OF THE INVENTION

According to the invention there is provided a closed loop system for collecting desired embryos from the uterus of a mammal. The apparatus of the system employs a closed container of a special liquid medium which is compatible with the embryos to be collected. Connected via conduits to the container is a pressure device such as a syringe which is used to draw a small quantity of liquid from the container. Another conduit is connected to a catheter which can be inserted into the uterine cavity to be flushed with liquid from the syringe. Liquid containing flushed out embryos is passed via a further conduit to a filter chamber, and the strained, filtered liquid returns to the container from which it can be redrawn by the syringe to repeat the flushing procedure. Suitable valves or clamps are provided in the several conduits to route the liquid medium from container to syringe to uterine cavity to the filter chamber and back to the container, in a closed loop.

The invention affords several advantages: 1. The new closed loop retrieval system is simple and inexpensive. 2. The system can be practiced by paraprofessionals and by relatively unskilled persons. 3. The total volume of liquid medium required is reduced, being only a small fraction of the amounts heretofore required for uterine flushing. By repetitive use, the smaller quantity of liquid is more effective than the larger quantity heretofore used. 4. Likelihood of loss of flushed out embryos is reduced resulting in a greater yield of embryos. 5. Potential for contamination of the liquid medium is reduced. 6. Concentration of the collecting fluid is rapid, and the filtered embryos are held safely in the liquid solution in the filter chamber. 7. The need for separate pieces of equipment is reduced to a single closed loop comprising an array of valved conduits connecting a liquid medium container, a pressure device such as a syringe, and a catheter. 8. The system is adapted for any liquid flushing medium desired by the user of the system which may be, for example, in a prepackaged form. Moreover, the package or container may be of glass or plastic with a screw top, a serum type bottle, a flexible pouch, etc. 9. The system is simple, effective, time saving and economical in use of the materials and equipment and is more efficient and affords vast improvements over existing embryo collection systems.

These and other objects and many of the attendant advantages of this invention will be readily appreciated as the same becomes better understood by reference to the following detailed description when considered in connection with the accompanying drawings in which:

DESCRIPTION OF THE PREFERRED EMBODIMENTS

Figure 1:
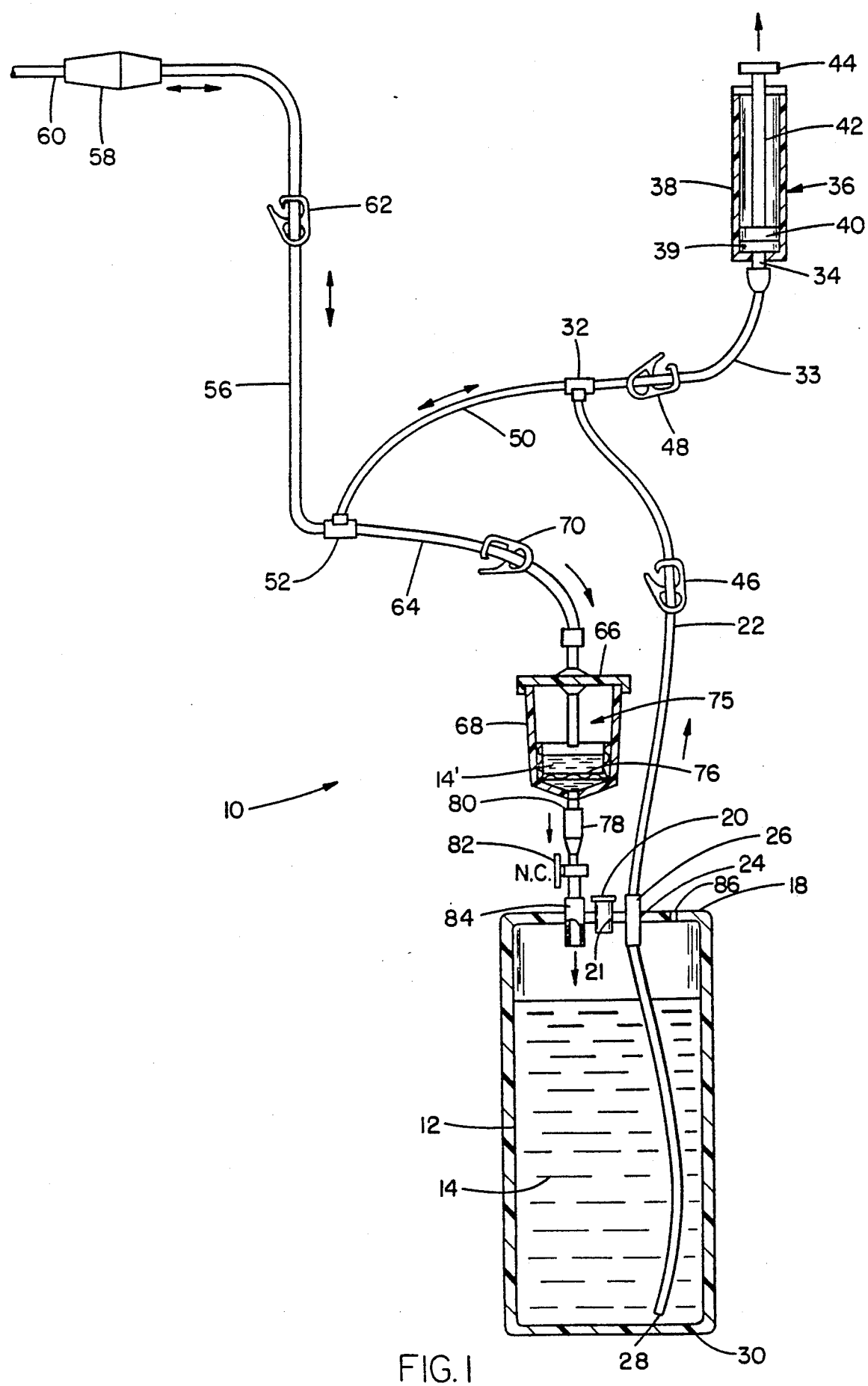
FIG. 1 is an elevational view, partially diagramatic in form of apparatus used in the system according to the invention, certain parts being shown in vertical section to show internal construction.

Referring now to the drawings, wherein like reference characters designate like or corresponding parts throughout, there is illustrated in FIG. 1 a closed loop apparatus designated generally by reference numeral 10. The apparatus 10 comprises a closed cylindrical container 12 which can be filled with a suitable liquid preparation of medium 14 for flushing a uterine cavity. The container 12 can be filled with a liquid medium 14 via an opening 21 in a top 18 of the container 12. The opening 21 is illustrated as closed by a stopper 20. A first flexible pipe or conduit 22 is secured in an opening 24 in the top 18 by a rubber bushing or sleeve 26. The conduit 22 has a bottom open end 28 located near a bottom 30 of the container 12. The conduit 22 extends upwardly to a first T-joint 32. A second conduit 33 is connected between one end of the T-joint 32 and an inlet end 34 of a syringe 36. The syringe has a tubular body 38 in which is an axially movable piston head 40 attacted to a plunger rod 42 terminating in a knob 44.

A pair of clamps or valves 46, 48 are mounted on flexible conduits 22 and 33 respectively for selectively opening and closing these conduits. A third flexible conduit 50 is connected between the T-joint 32 and another T-joint 52. A fourth flexible conduit 56 is connected to a suitable holder or coupling 58 for receiving and retaining one end of a catheter 60 which can be inserted into a uterine cavity to be flushed by the liquid medium 14. Another clamp or valve 62 is mounted on the conduit 56 for selectively opening and closing this conduit. A fifth flexible conduit 64 is connected between the T-joint 52 and the top 66 of a filter cap 68. A clamp or valve 70 selectively opens and closes the conduit 64. Inside a filter chamber 75 of the filter cap 68 is a screen 76 of sufficiently fine mesh to retain embryos discharged thereon. A nipple 78 is connected to an outlet 80 at the bottom of the filter chamber 75 below the screen 76. The nipple 78 is connected via a valve or stopcock 82 to an inlet coupling 84 at the top of the container 12. An air pressure release hole 86 can be provided in the top 18 of the container 12. Alternatively, the stopper can be loosened or removed at the hole 21 to relieve air pressure or suction during use of the syringe 36.

In operation of the apparatus 10, after the container 12 is filled with the liquid medium 14 to a desired level, a plunger rod 42 can be axially retracted in the syringe body 38. This will cause a suction in a chamber 39 below the piston head 40. The clamps 46 and 48 will be opened and the clamps 62 and 70 will be closed along with the valve 82. The liquid 14 will be drawn up into the syringe body under suction via conduits 22 and 33. Then the clamp or valve 46 will be closed. The catheter 60 will be inserted into a uterine cavity to be flushed for collecting any embryos therein. The clamp or valve 62 will then be opened and the syringe plunger 40, will be advanced to drive the liquid 14 under pressure, and out of the syringe 36 via conduits 48, 50 and 56, and the catheter 60 into the uterine cavity. The closed clamp or valve 70 and the valve 82 will then be opened and the valves 46 and 48 will be closed while the liquid 14 in the uterine cavity which is being flushed returns, gravitationally helped by contraction of the uterus, which may have expanded upon injection of the liquid 14 by the syringe 36. The returning liquid will flow through the conduits 56 and 64 into the filter cap 68. The liquid 14 will drain through the screen 76 which will retain any embryos while the excess liquid 14 flows back to the container 12. The valve 82 will then be closed to retain a sufficient volume of liquid 14' above and below the screen 76 to keep the collected embryos on the screen 76 in wet condition.

Immediately thereafter, the clamps 62 and 70 will be closed and the clamps 46 and 48 will be opened and the syring 36 will be operated again to draw liquid 14 under suction out of the container 12 to fill the syringe 36. Then the entire closed loop cycle will be repeated by closing the clamps 46 and 48 and opening the clamps 62, 70 and the valve 82 to flush the uterine cavity again and for discharging embryos collected thereby into the filter chamber 75. This cycle of flushing, filtering and returning excess liquid to the container 12 can be repeated as many times as desired. Ten cycles, for example, can be repeated in a very short time while the liquid circulates in the closed loop of conduits. The operation is very efficient, collecting a maximum number of live embryos in minimum time. It will be noted that a small volume of liquid medium 14, for example, about 80 cc. can be used repeatedly to perform the flushing operation heretofore performed by use of a liter or more of flushing medium. The closed filter chamber 75 prevents contamination of the collected embryos and the closed container, syringe and associated loop of conduits prevent contamination of the liquid medium at all times. No special skill is required to operate the apparatus. It is relatively simple and inexpensive, so that it can be discarded after an animal is treated. This will insure that an antiseptic sterile apparatus is always used, and one will not be used for more than one animal.

Summary of Cyclical Operation of the Apparatus 1. Aspiration of liquid medium 14 from container: 12 to syringe 36 valves 46 and 48 open;
valves 62, 70 and 82 closed.

2. Expulsion of liquid medium from syringe to uterine cavity valves 48 and 62 open;
valves 46, 70 and 82 closed.

3. Filtration of liquid medium drained from uterine cavity valves 62, 70 and 82 open;
valves 46 and 48 closed.

4. Control of quantity of liquid medium 14' retained in filter 68 valves 62 and 70 open;
valves 46, 48 and 82 closed.

Figure 2:
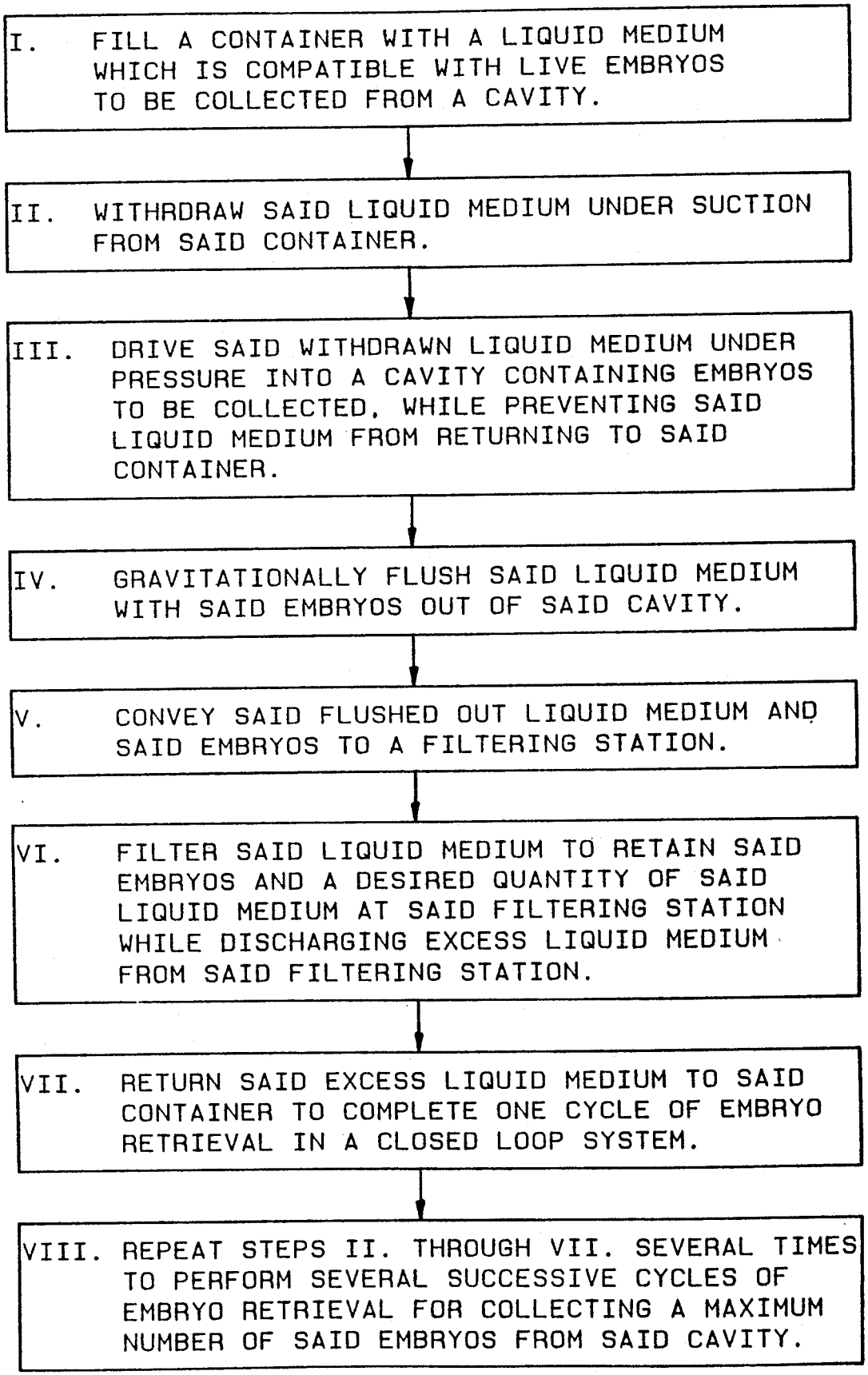
FIG. 2 is a flow chart of the method practiced in the system according to the invention.

FIG. 2 sets forth the steps I through VIII of the cylical method according to the invention. In step I, container 12 is filled with liquid medium 14. In step II, the liquid medium is withdrawn under suction from the container by operating the syringe 36. In step III, the withdrawn liquid is driven under pressure into a cavity containing embryos to be retrieved, while the liquid is prevented from returning to the container 12. In step IV, the liquid medium flushes embryos out of the cavity. In step V, the flushed out liquid medium and embryos are drained to the filter 68. In step VI, the embryos are collected in the filter 68 along with a desired amount of the liquid medium 14', and the excess liquid medium is discharged from the filter. In step VII, the excess liquid medium is returned from the filter to the container 12 to complete one cycle of embryo retrieval. In step VIII, the cycle outlined in steps II through VII is repeated as many times as necessary to retrieve the maximum possible number of embryos from the cavity.

It should be understood that to foregoing relates to only a limited number of preferred embodiments of the invention which have been by way of example only, and that is intended to cover all changes and modifications of the examples of the invention herein chosed for the purposes of the disclosure which do not constitute departures from the spirit and scope of the invention.

What is claimed is:

1. Apparatus for cyclically retrieving embryos form a uterine cavity, comprising:
    a container for a liquid medium compatible with live embryos;
    pressure means for withdrawing said liquid medium from said container and drivng said medium under pressure into said cavity;
    a filter for straining said liquid medium flushed out of said cavity and collecting any embryos from said liquid medium; and
    a plurality of conduits connected in a closed loop array between said container, said pressure means and filter for circulating said liquid medium cyclically into and out of said container, pressure means, cavity and filter to collect said embryos in said filter.

2. Apparatus as defined in claim 1, further comprising valves at certain ones of said conduits for controlling direction of flow of said liquid medium into and out of said container, pressure means, cavity and filter.

3. Apparatus as defined in claim 1 wherin said pressure means comprises a syringe.

4. Apparatus as defined in claim 2 wherein said valves are spring clamps manually operable to open and closed said certain conduits.

5. Apparatus as defined in claim 2, further comprising outlet conduit means connected between said filter and said container and valve means at said outlet conduit means for retaining a desired quantity of said flushed out liquid medium in said filter to keep any embryos thereat immersed therein.

6. Apparatus as defined in claim 5, further comprising coupling means at one of said conduits adapted to engage a catheter thereat for conveying said liquid medium into and out of said cavity.

7. Apparatus for cyclically retrieving embryos from a uterine cavity, comprising:
- a container for a liquid medium compatible with live embryos;
- a syringe for withdrawing said liquid medium by suction from said container and for driving said withdrawn liquid medium under pressure into said cavity;
- a first conduit terminating at one end in said container to convey said liquid medium therefrom;
- a first T-joint connected to the other end of said conduit;
- a second conduit connected between said T-joint and said syringe for conveying said liquid medium into and out of said syringe;
- a second T-joint;
- a third conduit connected between said first and second T-joints;
- a fourth conduit connected to said second T-joint for conveying said liquid medium under pressure from said syringe to said cavity via said second and third conduits, and for conveying said liquid medium flushed out of said cavity back to said container;
- a filter for straining said liquid medium flushed out of said cavity for collecting any embryos retrieved from said liquid medium flushed out of said cavity;
- a fifth conduit connected between said second T-joint and said filter for conveying said liquid medium flushed out of said cavity to said filter; and
- outlet conduit means connected between said filter and said container for conveying excess strained liquid medium to said container; and
- whereby repeated operation of said syringe will cause said liquid medium to circulate cyclically into and out of said container, syringe, cavity, and filter via said conduits to concentrate said embryos in said filter.

8. Apparatus as defined in claim 7, further comprising a plurality of valves at said first, second, third, fourth and fifth conduits respectively for controlling direction of flow of said liquid medium into and out of said container, syringe, cavity and filter.

9. Apparatus as defined in claim 7, comprising a further valve at said outlet conduit means for retaining a desired quantity of said flushed out and strained liquid medium in said filter to keep said embryos immersed therein.

10. Apparatus as defined in claim 9, further comprising coupling means connected to said fourth conduit adapted to engage a catheter thereat for conveying said liquid medium into and out of said cavity.

11. A method for collecting embryos in a closed loop system, comprising the successive steps of:
- A. filling a container with a liquid medium which is compatible with live embryos to be collected from a cavity;
- B. withdrawing said liquid medium under suction from said container;
- C. driving said withdrawn liquid medium under pressure into said cavity conatining embryos to be collected, while preventing said liquid medium from returning to said container in said loop;
- D. flushing said liquid medium with said embryos out of said cavity;
- E. conveying said flushed out liquid medium and said embryos directly to a filtering station;
- F. straining said liquid medium to retain said embryos and a desired quantity of said liquid medium at said filtering station, while discharging excess liquid medium from said filtering station; and
- G. returning said strained excess liquid medium to said container directly from said filtering station to complete one cycle of embryo retrieval in said closed loop system.

12. A method for collecting embryos as defined in claim 10, comprising the further steps of repeating said steps B. through G. in sequence several times to perform several successive cycles of embryo retrieval, for collecting a maximum number of said embryos from said cavity.

* * * * *